United States Patent
Strobel et al.

(10) Patent No.: US 6,660,263 B2
(45) Date of Patent: Dec. 9, 2003

(54) OOCYDIN AND METHODS OF USE FOR PROTECTION OF PLANTS FROM OOMYOCYTE PATHOGENS

(75) Inventors: Gary A. Strobel, Bozeman, MT (US); Jia Yao Li, San Francisco, CA (US)

(73) Assignee: HMV Corporation, Alpine, UT (US)

( * ) Notice: Subject to any disclaimer, the term of this patent is extended or adjusted under 35 U.S.C. 154(b) by 0 days.

(21) Appl. No.: 09/858,871

(22) Filed: May 17, 2001

(65) Prior Publication Data

US 2002/0032308 A1 Mar. 14, 2002

Related U.S. Application Data

(60) Provisional application No. 60/205,102, filed on May 18, 2000.

(51) Int. Cl.[7] ............................ A01N 63/00; C12P 1/00; C12P 21/04; C12N 1/00
(52) U.S. Cl. ..................... 424/93.46; 435/41; 435/71.2; 435/243; 435/880
(58) Field of Search ................... 424/93.46; 435/41, 435/71.2, 243, 880

(56) References Cited

U.S. PATENT DOCUMENTS 5,869,038 A    2/1999  Leifert et al.
6,060,051 A  * 5/2000  Heins et al.

OTHER PUBLICATIONS

Strobel et al. Microbiology, 1999, 145: 3557–3564.*

Stedman's Medical Dictionary, 1995. (Williams and Wilkins, Baltimore, p. 1443.*

C.H. Hassal, et al. The Conformation of Serratamolide and Related Cyclotetradepsipeptides in Solution, Phys. Org., pp. 1757–1761.

* cited by examiner

Primary Examiner—Christopher R. Tate
Assistant Examiner—Kailash C. Srivastava
(74) Attorney, Agent, or Firm—McDermott, Will & Emery

(57) ABSTRACT

Oocydin A is a mono-chlorinated lipophilic macrocyclic lactone that was isolated from a strain of *Serratia marcescens* that produces oocydin A in culture. Oocydin A has a molecular mass of 470, contains one atom of chlorine, a carboxyl group, and a tetrahydrofuran ring internal to a larger macrocyclic ring. Minimum inhibitory concentrations of circa 0.03 $\mu g\ ml^{-1}$ were noted for oocydin A against phytopathogenic Oomycetes. Oocydin A can be used as an anti-Oomycete in agricultural applications for crop protection.

8 Claims, 1 Drawing Sheet

Oocydin

OOCYDIN AND METHODS OF USE FOR
PROTECTION OF PLANTS FROM
OOMYOCYTE PATHOGENS

CLAIM OF PRIORITY

This application claims priority to U.S. provisional patent application Ser. No. 60/205,102, filed May 18, 2000.

FIELD OF THE INVENTION

This invention relates generally to the protection of plants from pathogen attack, and particularly to protection from Oomycete pathogens.

BACKGROUND OF THE INVENTION

One of the largest problems facing agriculture today is effective control of plant pathogens. Compounds that are biologically derived and toxic only to specific target organisms are preferred for control of plant pathogens, because of their decreased impact on the environment and on non-target organisms.

Plants, especially those growing in freshwater environments, must have disease resistance mechanisms to cope with aquatic plant pathogenic organisms that may invade and destroy them. Oomycetes would be expected to attack plants that normally exist in strictly aquatic environments. However, aquatic plants seem to thrive and be relatively disease free in these ecosystems. This biological conundrum may be related to extrinsic factors controlling plant disease resistance. Epiphytic or endophytic microbes may associate with aquatic plants and produce antioomycetous compounds. If such compounds exist, they may prove agriculturally applicable to plant disease control situations in which Oomycetes are a problem.

Metalaxyl is well established as the agent to which the Oomyctes are the most sensitive. However, increasing resistance to metalaxyl is developing in certain Oomycete populations and this agent is being rendered increasingly less effective. Lyr, H., *Modern Selective Fungicides* (Gustav Fischer Verlag: New York, Jena., 1995). Thus, a need exists for new compounds to combat these plant pathogens.

SUMMARY OF THE INVENTION

The invention provides oocydin A, a mono-chlorinated lipophilic macrocyclic lactone possessing selective antioomycetous activity against Oomycete plant pathogens.

The invention also provides *Serratia marcescens* MSU-97, an isolate that produces oocydin A into culture medium. The invention thus provides a method of making and purifying oocydin A.

The invention further provides an environmentally desirable method of controlling and preventing Oomycete infestation of plants by administering the compounds of the invention to plants.

DETAILED DESCRIPTION OF THE INVENTION

Figure 1:
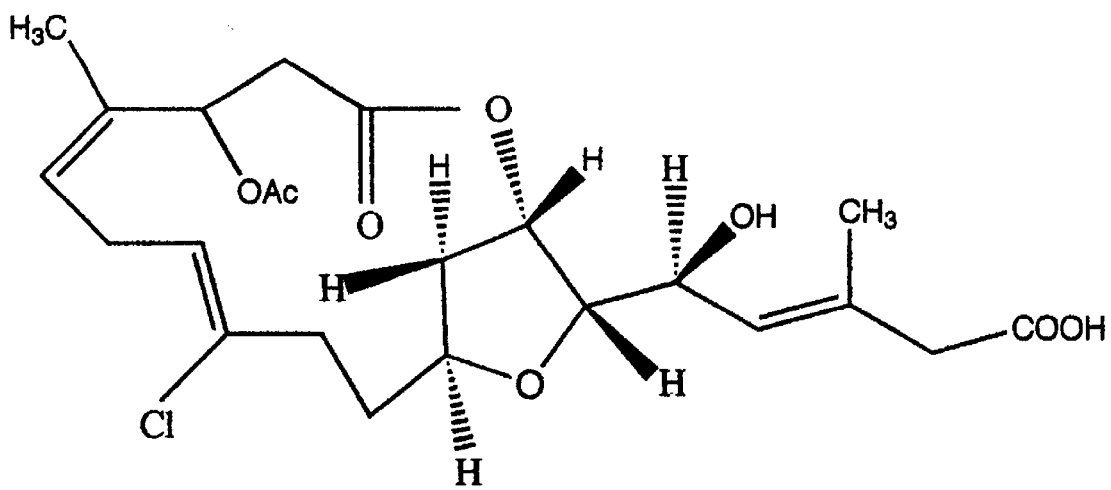
FIG. 1 shows the structure of oocydin A (no absolute stereochemistry is implied).

*Serratia marcescens* MSU-97. *Serratia marcescens* is a Gram-negative bacillus that occurs naturally in soil and water, as well as in the human intestines. Methods of identifying and classifying S. marcescens are known in the art. Falkiner FR (1997) *J Med. Microbiol.* 46:903–12. Growth of *Serratia marcescens* is accompanied by the production of a characteristic red tripyrrole pigment called prodigiosin. The production of a number of secondary metabolites is correlated with pigment synthesis. Prodigiosin is synthesized from amino acids, although the complete biosynthetic pathway is unknown. Bermingham, M. A., et al. (1971). *J Gen. Microbiol.* 67, 319–324.

*Serraria marcescens* isolate 97 (MSU-97) is an epiphytic bacterium isolated from *Rhyncholacis pedicillata*, an aquatic plant native to Venezuela. See, EXAMPLE 1. A biologically pure culture of *Serratia marcescens* MSU-97 is deposited in the culture collection at Montana State University. A viable deposit containing *Serrafla marcescens* MSU-97, has been deposited with the CENTRAALBUREAU VOOR SCHIMMEL CULTURES Institute of the Royal Netherlands Academy of Arts and Sciences. (CBS). The Netherlands. and has been assigned Accession No. CBS 112860. The original deposit was made Oct. 10, 1998 and converted to a deposit under the regulations of the Budapest Treaty on May 27, 2003. The subject cultures are deposited under conditions that ensure that access to the cultures will be available during the pendency of the patent application disclosing them to one determined by the Commissioner of Patents and Trademarks to be entitled thereto under 37 C.F.R. §1.14 and 35 U.S.C. §122. The deposits are available as required by foreign patent laws in countries where counterparts of the subject application, or its progeny, are filed. However, the availability of a deposit does not constitute a license to practice the subject invention in derogation of patent fights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least 30 years after the date of deposit or for the enforceable life of any patent which may issue disclosing the cultures plus 5 years after the last request for a sample from the deposit. The depositor acknowledges the duty to replace the deposits should the depository be unable to furnish a sample when requested, due to the conditions of the deposits. All restrictions on availability to the public of the subject culture deposits will be irrevocably removed upon granting of a patent disclosing them.

Compounds of the invention. A mono-chlorinated lipophilic macrocyclic lactone, oocydin A (FIG. 1), was isolated from *Serratia marcescens*. In culture, *Serratia marcescens* MSU-97 produces oocydin A that can be recovered from the culture medium. Oocydin A has a molecular mass of 470, contains one atom of chlorine, a carboxyl group, and a tetrahydrofuran ring internal to a larger macrocyclic ring.

Minimum inhibitory concentrations (MICs) of circa 0.03 $\mu$g ml$^{-1}$ were noted for oocydin A against such phytopathogenic Oomycetes as *Phytophthora parasitica, P. cinnamomi,* and *P. citrophora.* See, EXAMPLE 2. Overall, it appears that oocydin A has selective lethal activity against Oomycetes at MICs lower or similar to those noted for metalaxyl. Oocydin A can thus be used as an anti-Oomycete in agricultural applications and especially for crop protection.

Oomycetes. The Stramenophila have recently been classified as being a new kingdom of plants. Among the Stramenophila are the Labyrinthulomycota, which have a thallus that is a network of branched tubes within which amoeboid cells crawl. Also among the Stramenophila are the Hyphochytriomycota, which have a thallus that is single-celled or rhizoidal and have motile cells with a single anterior tinsel type flagellum. The Oomycetes are the largest group of Stramenophila. Oomycetes have a thallus that is filamentous with coenocytic hyphae or rarely single-celled or holocarpic. Oomycetes have motile cells, often with whiplash and tinsel flagellae.

There are more than 500 species in the Oomycetes. The Oomycetes include such genera as Leptomitus, Brevilegnia, Aphanomyces, Achlya, Saprolegnia, Pythium, Plasmopara, Phytophthora, and Peronospora.

The Oomycetes that have undergone extensive life cycle studies have been found to be diploid in the vegetative phase with meiosis occurring during gametogenesis. "Oomycota" means "egg fungi", a term that refers to the large round oogonia, or structures containing the female gametes. Oomycetes are oogamous, producing large non-motile gametes called eggs, and smaller gametes called sperm.

The Oomycota were once classified as fungi, because of their filamentous growth, and because they feed on decaying matter like fungi. The cell wall of Oomycetes, however, is not composed of chitin, as in the fungi, but is made up of a mix of cellulosic compounds and glycan. The nuclei within the filaments are diploid, not haploid as in the fungi.

Oomycetes are found all over the world in fresh-water and salt-water habitats. Oomycetes absorb their food from the surrounding water or soil, or may invade the body of another organism to feed. The presence of free water or high humidity is important for the development and the pathogenicity of these organisms. Some of the terrestrial Oomycetes are among the most important plant pathogens.

Many Oomycetes are important parasites on flowering plants. These include root rotting fungi, seedling dampening mold, blister rusts, white rusts (Albugo, such as *A. candida*), water molds and the downy mildews (including *Peronospora tabacina*) that attack mainly potatoes, tomatoes, vines, hops, maize, sugar beet, tobacco, vegetables, lettuce, but also bananas, rubber, as well as lawns and ornamentals. Plant diseases caused by Oomycetes can have a major impact on human populations. *Plasmopara viticola* causes the downy mildew of grapes that, in the late 1870s, almost wiped out the French wine industry. *Phytophthora infestans* causes the late blight of potato that, in the summer of 1846, caused the great Irish Potato Famine.

Other species of Phytophthora destroy eucalyptus, avocado, pineapples, and other tropical crop plants. *Phytophthera parasitica* causes black shank disease. Root rot of ornamental plants, such as poinsettia, can be caused by *Pythium aphanidermatum, P. debaryanum, P. irregular, P. megalacanthum, P. oligandum, P. perniciorum, P. polymastum* and *P. utimum*, and by *Phytophthora parasitica*.

Accordingly, the compounds of the invention and the methods of using the compounds are useful for protecting or treating Oomycete-related diseases affecting cereals (maize, wheat, barley, rye, oats, rice, sorghum and related crops); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (marrows, cucumber, melons); fiber plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as tobacco, nuts, coffee, sugar cane, tea, vines, hops, bananas and natural rubber plants, as well as ornamentals (flowers, shrubs, broad-leaved trees and evergreens, such as conifers). This list does not represent any limitation.

Administration of the Compounds of the Invention. The invention offers a number of advantages and uses stemming from the easily controlled administration of the compound of the invention on in plants or plant tissue, such as in the manner of U.S. Pat. Nos. 5,856,154, 6,031,153, and 6,228,884. Administration may be accomplished simply by applying the compound of the invention to the plant tissue, or to the plant or part of the plant in such a manner and in such an amount as to be effective. For example, application of the compound of the invention can be made to the entire plant (i.e., stem and both sides of the leaves). If administration to the roots is desired, application to the seeds or the soil around the seeds or roots is also possible.

The compounds of the invention can be applied in pure form, in solution or suspension, as powders or dusts, or in other conventional formulations used agriculturally or in bioreactor processes. See, U.S. Pat. No. 5,856,154. The compounds of the invention can be prepared in formulations in a known manner, for example by intimately mixing and/or grinding the active ingredients with extenders, such as, for example, with solvents, solid carriers and, if appropriate, surface-active compounds (surfactants). See, U.S. Pat. No. 6,228,884. Suitable carriers and additives can be solid or liquid and correspond to the substances expediently used in formulation technology, such as, for example, natural or regenerated mineral substances, solvents, dispersants, wetting agents, tackifiers, thickeners, binders or fertilizers. See also, U.S. Pat. No. 6,228,884. Such formulations may include solid or liquid carriers, that is, materials with which the regulator is combined to facilitate application to the plant, tissue, cell or tissue culture, or the like, or to improve storage, handling or transport properties. Examples of suitable carriers include silicates, clays, carbon, sulfur, resins, alcohols, ketones, aromatic hydrocarbons, and the like. If formulated as a conventional wettable powder or aqueous emulsion, the regulator formulation may include one or more conventional surfactants, either ionic or non-ionic, such as wetting, emulsifying or dispersing agents.

As a liquid formulation the compounds of the invention may be applied as a spray to plant leaves, stems or branches, to seeds before planting or to the soil or other growing medium supporting the plant. Alternatively, the administration of the compounds of the invention can be guided by the administration of acylalanine fungicides, such as metalaxyl (N-(2,6-dimethylphenyl)-N-(methoxyacetyl)-DL-alanine methyl ester); benalaxyl (N-(2,6-dimethylphenyl)-N-(phenylacetyl)-DL-alanine methyl ester); furalaxyl (N-(2,6-dimethylphenyl)-N-(2-furanylcarbonyl)-DL-alanine methyl ester). The preferred application of the acylalanine fungicides is foliar application, in which the foliage and the growing plant being treated with the active ingredient. See, U.S. Pat. No. 6,228,884. In the case of soil application, the active ingredient is incorporated into the soil directly by applying it in liquid form, or, for example, by means of granules.

A preferred method of applying the compounds of the invention is to the aerial parts of the plant, especially the foliage (foliar application). See, U.S. Pat. No. 6,228,884. Number and rate of application depend on the biological and climatic environmental conditions for the pathogen. Alternatively, the compounds of the invention can reach the plant via the soil through the root system (systemic action), by drenching the site of the plant with a liquid composition or by incorporating the substances into the soil in solid form, for example in the form of granules (soil application).

The compounds of the invention are employed as pure active ingredient or, preferably, together with the adjuvants conventionally used in the art of formulation and is therefore processed in a known manner to give, for example, emulsion concentrates, spreadable pastes, directly sprayable or dilutable solutions, dilute emulsions, wettable powders, soluble powders, dusts, granules, or by encapsulation, for example in polymeric substances. The methods of application, such as spraying, atomizing, dusting, scattering, brushing on or pouring, as well as the type of the compositions, are selected to suit the intended aims and the prevailing circumstances.

As a rule, the agrochemical compositions comprise 0.1 to 99%, in particular 0.1 to 95%, of the active ingredient 99.9 to 1%, in particular 99.9 to 5%, of a solid or liquid additive, and 0 to 25%, in particular 0.1 to 25%. See, U.S. Pat. No. 6,228,884. While concentrated compositions are more preferred as commercially available goods, the end consumer uses, as a rule, dilute compositions.

It is a standard demand in crop protection to achieve an optimal effect with an active ingredient at the lowest dosage rate required while simultaneously keeping the pollution of the environment as low as possible. For in vitro application, the compound of the invention is added quite easily, for example, by applying the compound of the invention to the medium contacting the plant cells. In bioreactor systems, administration can be achieved by a single addition of regulator formulation to the reaction medium or by gradual addition over a predetermined period of time.

One advantage arises from the ability to apply the compound of the invention during different times of plant development. For example, the synchronization of the application of the compound of the invention with plant development (germination, tillering, sprouting, flower formation, anthesis, fruit ripening, dry down, abscission etc.) can be accomplished.

The compounds of the invention can also be applied to plants in combination with another agent that may afford some benefit to the plant. For example, the compounds of the invention can be admixed with a fertilizer and then applied.

The details of one or more embodiments of the invention are set forth in the accompanying description above. Although any methods and materials similar or equivalent to those described herein can be used in the practice or testing of the invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The following EXAMPLES are presented in order to more fully illustrate the preferred embodiments of the invention. These examples should in no way be construed as limiting the scope of the invention, as defined by the appended claims.

EXAMPLE 1

*Serratia Marcescens* MSU-97

Isolation of *Serratia marcescens* MSU-97. *Rhyncholacis pedicillata* is a small highly specialized aquatic plant of the family Podostemaceae that grows in colonies and thrives in some of the brown-black rivers of the Venezuelan-Guyana. *R. pedicillata* is 0.2–1.0 m in size and it has a bulbous base that anchors the plant to a rock. Its stems are multibranched, are lacy-like, and covered with numerous small leaves.

Close examination of individual plants in the Carrao River revealed animal or environmentally inflicted wounds on the stems. Normally, such wounds would serve as entry points for one or more pathogenic Oomycetes. However, little or no disease symptoms on the plants are observed.

Several small stem fragments of *R. pedicillata* were removed from the plant growing in its river environment and cut into pieces about 5.0 mm. These tissue pieces were then soaked overnight in 0.1M sodium phosphate buffer (pH 6.8) made 0.1 M with respect to NaCl. After 12 hr, the saline solution was collected, left at 23° C. for 1 hr and then streaked onto a semi-selective medium (King's B (KB)) according to the procedures of Miller, C. M. et al. (1998). *J. Appl. Microbiol.* 84,937–944.

After 2 days, the most commonly appearing colonies consisted of bacilliform bacteria that were producing a bright red pigment. The red-pigment producing bacterial strain was identified as *Serratia marcescens*. Standard isolates of *S. marcescens*, used for comparative purposes, were obtained from the MSU bacterial culture collection, Dept of Microbiology, Montana State University, Bozeman, Montana.

Each of these colonies was transferred back to the KB medium and incubated for several days prior to being transferred as individual colonies onto potato dextrose agar plates (PDA). These PDA plates were incubated for at least 3–5 days at 23° C. prior to having the PDA plate co-inoculated (as 5.0×5.0 infested agar plugs) with a rapidly growing culture of *Pythium ultimum*. The co-inoculated culture plates were then incubated at 23° C. and examined for antioomycetous activity. Bacterial colonies producing zones of inhibition around them were considered positive for antioomycetous activity.

Several antioomycetous activity-producing bacteria were isolated from *R. pedicillata*, but *S. marcescens* was by far the most prevalent. One isolate *S. marcescens* (MSU-97) of produced impressive zones of inhibition when challenged with *P. ultimum* in plate bioassay tests. Inhibition zones were retained on the plates at 23° C. until the agar in the plate desiccated (after 4–6 weeks). *P. ultimum* did not develop any further on the plates when challenged with isolate 97 than that of its original zone of inhibition appearing after 2–3 days.

Our isolate of *S. marcescens* is stored in the Montana State University bacterial culture collection and assigned Accession No. 2271 and is stored in CBS under Accession No. CBS 112860.

Since *S. marcescens* is a relatively common microorganism. Regular isolates of it were also screened in the antioomycetous plate test. Neither ATCC isolate 1009, nor MSU isolate 69 demonstrated any antioomycetous activity diffusing from the culture after 3 days of exposure to *P. ultimum*. This straightforward antifungal test revealed that the likelihood of finding one or more novel antioomycetous substances from isolate 97 of *S. marcescens* was extremely likely.

Scanning electron microscopy. Materials to be examined were placed in 2% glutaraldehye in 0.1 M sodium cacodylate buffer (pH 7.2–7.4) (Upadhyay, R. V. et al. (1993). *Mycol. Res.* 95, 785–791). The samples were critical point dried, gold coated with a sputter coater and observed and photographed with a JEOL 6100 scanning electron microscope. Bacterial preparations were supported on dried γ-irradiated carnation leaves that served as a support for the cells.

SEM examination of the surface of some small stems of R. pedicillata revealed that bacterial colonies were in abundance. Hundreds of individual cells seemed to constitute each colony. Individual bacterial cells also appeared on the plant surface. Serratia marcescens* colonized the surface of the stems of *R. pedicillata,* in contrast to being internal to them.

The surface characteristics of the bacteria on the plant were identical to those on bacterial surfaces of pure cultures of authentic *S. marcescens* (isolate 97). The bacterial surface characteristics included multiple small projections as well as a generally relatively rough cell surface. This does not appear to be common in bacteria and this characteristic may serve as a means to help locate and identify *S. marcescens* on the surface of its host. In addition, the size and shape of the bacterial cells on the plant and those of the authenticated culture appear to be identical. Since *S. marcescens* was primarily recovered from the plant surface and not from internal tissues, it was considered more epiphytic than endophytic in its relationship to the plant.

EXAMPLE 2

Oocydin A is a Chlorinated Macrocyclic Lactone With Potent Antioomycetous Activity This EXAMPLE deals primarily with the isolation and the chemical characterization of oocydin. Some specific details are also given on the biological activity of oocydin and its relationship to the biology of the plant-microbe relationship is discussed along with its potential usefulness to agriculture.

Oocydin Isolation Procedures. Cells from a single colony of *S. marcescens* no. 97 were used to inoculate 15 ml of PD broth and the culture was grown overnight with shaking at 23° C. This culture was then used to inoculate 2800 ml flasks, each containing 1 L of the following: 24 g PD; 6 g soytone; 4 g yeast extract and 100 mg NaCl. The cultures were incubated under still conditions at 23° C. for 15 days. As an example, the culture fluid of one flask was extracted twice with two equal volumes of methylene dichloride and this solvent taken to dryness by flash evaporation at 45–50° C. under vacuum. Approximately, 2.1 g of residue was present after evaporation of the solvent.

The resulting material was then dissolved in chloroform and placed on a 3.0×20.0 cm column of silica gel. The column was eluted with a chloroform:methanol 10:1 v/v solution. The first 100 ml to elute from the column was discarded and the next 50–100 ml (approximately 650 mg) contained the antioomycetous activity (see, bioassay below). This material was then placed onto another silica gel column (the same size as initially used) and eluted with methylene dichloride: methanol solution 10:1 v/v. Here, the first 50 ml of eluting solution were discarded and the next 80 ml contained the bioactivity (approximately 50–60 mg).

The mixture of compounds was then subjected to successive series of preparative thin layer chromatographic (TLC) steps to yield a pure product. All solvents used for TLC were HPLC grade. All TLC was conducted on EM-Merck precoated glass silica gel plates at a thickness of 0.25 mm. The compounds were applied to 20×20 cm silica gel plates (0.25 mm thickness) and the solvents permitted to run nearly the full length of the plate. The solvents were as follows: Solvent A) chloroform: methanol: acetic acid 12:1: 0.1 v/v/v; Solvent B) chloroform: methanol: acetic acid 6:2:0.1 v/v/v; and Solvent C) methylene dichloride: methanol 6:2 v/v. After each successive TLC step, the compound possessing bioactivity (see bioassay procedure described below) after elution of each band on the plate with methanol was reapplied to the next plate prior to separation.

In Solvent System A, the compound appeared at an $R_F$ value of 0.49. In solvents consisting of methylene dichloride: methanol 6:2 v/v it was 0.65; the $R_F$ value in chloroform:methanol:ammonia hydroxide 6:2:0.1 v/v/v was 0.34; and in chloroform: methanol 7:1 v/v was 0.27. In each case, after spraying with the vanillin sulfuric acid reagent only one spot appeared on the plate. Once obtained and authenticated, a small amount of oocydin was applied at the margin of the TLC plate as an appropriate reference for larger scale preparations. The bioactive compound appeared as a brownish spot, with the vanillin-sulfuric reagent, after gentle heating (Cardellina, J. H. (1991) *J. Chromatogr.* 14, 659–665).

Ultraviolet Spectroscopy. Furthermore, no other UV absorbing or UV fluorescent spots appeared on the plates after examination in long and short wavelength UV. The ultraviolet absorption spectrum of oocydin was taken in 1 ml of 100% methanol (1.0 cm light path).

Yield. Approximately 15–18 mg of oocydin was recovered per liter of culture fluid. It was obtained as a whitish powder by dissolving it in a methanolic-aqueous solution, freezing and subjecting it to lyophilization.

This was the preparation that was subjected to physical, chemical, and biological characterization, once the purity of the sample was firmly established. The oocydin was first subjected to TLC and HPLC tests to check for its purity.

High performance liquid chromatograpy (HPLC). The putative TLC purified sample of oocydin was subjected to HPLC by placing it on an Altima C-18 column (7.0 mm×250 mm) (Alltech, Deerfield, Ill.) and eluting in a linear gradient fashion starting with 30% acetonitrile in water with 0.1% TFA and mixing with 50% acetonitrile in water with 0.1% TFA over the course of 30 min. All solvents used for HPLC were HPLC grade. Detection was performed with a Waters variable wavelength detector at 208 λ.

After HPLC analyses under the conditions described only one peak, absorbing at 208 nm appeared and it had a retention time of 19.7 min. Upon collection of the contents of this peak and subjection to the bioassay test it was active against *P. ultimum.* Collectively, these chromatographic data suggested that the antioomycetous agent of S. marcescens isolate 97 is homogeneous enough for spectroscopic and chemical analyses.

Melting point. The uncorrected melting point of oocydin A is 106–108 C.

Mass Spectroscopy. After the purity of oocydin was established, it was subjected to a series of analyses using standard spectroscopic techniques. Electrospray mass spectroscopy was performed by dissolving the sample in methanol: water: acetic acid 50:50:1 v/v/v. The sample was then injected into a mass spectrometer with a spray flow of 2 μl $min^{-1}$ and a spray voltage of 2.2 Kv via the loop injection method. Oocydin was also subjected to laser desorption mass spectroscopy on a Perspectives Biosystems Instrument, Cambridge, Mass. The sample was incorporated into a matrix of 3,5 dihydroxy benzoic acid and scanned accordingly. The following parameters were used: Acclerating voltage 30,000 volts, grid voltage 70%, mirror ratio of 1.06, laser 260 and 260 and cytochrome c were used to standardize the instrument. Negative high resolution FAB mass spectroscopy was done as a confirmation of elemental analysis. Degradative techniques of elemental analysis were used at the Atlantic Microlab of Norcross, Ga. and the C, H, and Cl contents were determined.

Electrospray mass spectroscopic analysis of oocydin A produced a major peak at 493.9 m/e. This is consistent with a single charged species of $(M+Na)^{+1}$. The laser desorption spectrum also produced a major peak at 493.3 consistent with $(M+Na)^{+1}$. However, there was also a significant M+2 peak at 495.3, that could be accounted for by oocydin A possessing a chlorine atom. This may be true because of a high abundance of the isotope $^{37}Cl$. Negative HRFAB data yielded M-H of 469.1640, which accounted for an empirical formula $(C_{23}H_{30}O_8Cl_1)$. The difference between the negative HRFAB data (469=MH$^+$) and the electrospray laser desorption data $(M=470+Na)^{+1}$ is equivalent to 23 mev which is the atomic weight of sodium. Therefore, in both the electrospray and laser desorption mass spectral analysis, oocydin A sequestered a sodium ion which accounted for its MW plus 23 mev. In addition, the molecule assumed a net positive charge by picking up H$^+$. Elemental analysis of oocydin for its halogen content revealed that it was equal to 7.1% (the expected Cl content is 7.4%). In the elemental analysis, the halogen was not specifically identified as chlorine. Although the negative HRFAB, and the laser desorption mass spectral data gave a strong indication for the presence of chlorine in oocydin A, these analyses were not totally definitive. Therefore, further supportive evidence for the presence of chlorine in oocydin A was obtained with an Oxford Inst Co. energy dispersive X-ray microanalysis system on a JEOL-SEM. The test was conducted on about 15–20 µg of oocydin A supported on an Al stub and subjected to x-ray analysis. A peak distinctive for chlorine, and no other halogen appeared in the spectrum. Thus, the empirical formula for oocydin A is $C_{23}H_{31}O_8Cl_1$.

Infrared Spectroscopy. Infrared spectroscopy was done on a Perkin Elmer instrument with oocydin imbedded in a matrix of anhydrous KBr and pressed into a pellet. Averages of 16 scans were taken on the sample.

The IR absorption band at 2982 cm$^1$ had a shoulder that suggested alkane and alkene functionalties, whereas, the intense band at 1713 cm$^{-1}$ indicated the presence of one or more acetate esters. Weaker bands at 1417 and 1602 cm$^{-1}$ suggested the presence of a carboxylate functionality. Other notable bands occurred at 1640, 1124, 1030, 902 and 835 cm$^{-1}$. The IR spectrum provided a data set unique to oocydin A and suggested the presence of certain functional groups.

Optical Rotation. The optical rotation of oocydin A was determined in a sample dissolved in 100% methanol and analyzed in a JASCO-P1010 instrument (Tokyo, Japan).

The optical rotation, taken on 2.2 mg of oocydin A dissolved in 1 ml of methanol at 589 nm is +18.2.

Nuclear Magnetic Resonance Spectroscopy. Oocydin was subjected to a multitude of Nuclear Magnetic Resonance (NMR) techniques after being dissolved in 100% deuterated methanol. Initially, the proton spectrum was obtained on a Bruker DRX 500 NMR with 64 scans with a delay cycle of 2 sec and collected as 32 k real points in time domain frequency of 500.13 MHz. The spectrum was referenced to the MeOD signal at 3.0 ppm.

For acquisition of the $^{13}C$ spectrum, 4096 scans were made with a recycle delay of 10 sec and collected as 32 k real time domain points using a transmitter frequency of 125.77 MHz. The spectrum was referenced to the residue MeOD signal at 49.0 ppm.

Oocydin A was also analyzed by 2D INADEQUATE analysis on a 500 MHz Varian Inova spectrometer operating at 125.892 MHz and 26° C. Oocydin A (58 mg) was dissolved in 200 µl of CDCl$_3$ and the analysis performed using a Varian 5 mm probe and a Shigemi microtube whose susceptibility was matched to the solvent used. Analysis parameters included a 10 µs $^{13}C$ 90° pulse and a pulse sequence delay optimized for detection of 55 Hz carbon—carbon scalar coupling constants. A total of 64 evolution increments of 800 transients each were used for an analysis time of 4.7 days. Digital resolution of the acquisition and evolution dimensions were 0.2 and 176.1 Hz per point, respectively.

The gross structure of oocydin was deduced from the various NMR data, particularly pulse field DQF-COSY, pulse field HMQC, pulse field HMBC and difference ID-NOE spectra in a JEOL JNM-alpha 600 spectrometer. Stereochemistry of oocydin was primarily determined by 1D-NOE and selective NOE assays. In addition, spectral processing and signal assignments were done in a near automated fashion using previously described software (Dunkel, R. et al., (1990) *J. Magn. Reson.* 90, 290–302; Dunkel, R. et al., (1992) *Anal. Chem.* 62, 3133–3149; Harper, J. K. et al., (1996) *J. Chem. Soc. perkin Trans.* 2, 91–100).

The proton NMR spectrum was consistent with a compound having methyl, methylene and hydrogen bonded on carbons bearing oxygen. In the $^{13}C$ NMR spectrum, it was possible to account for 23 carbon atoms. This NMR analysis also showed double bonded carbons, carbons bearing carbonyl groups, as well as methyl carbons.

While the one dimensional NMR spectra of oocydin A were instructive, the structure proposed for this compound is primarily based on the use of a collection of sophisticated NMR techniques each of which provided useful information on the relative positions of the atoms making up this compound. The carbon types were first determined with DEPT analysis, as described by Doddrell, D. M. et al. (1982) *J. Magn. Reson.* 48, 323–327. One bond and longer proton-carbon connections were established through HMQC and HMBC. Selective ROESY and NOE difference analyses allowed the relative stereochemical orientations to be established. A 2D INADEQUATE analysis was used to verify the proposed carbon—carbon connections. All INADEQUATE connections were determined using previously described data analysis software specifically suited to low signal-to-noise acqusitions (Dunkel, R. et al., (1990) *J. Magn. Reson.* 90, 290–302; Dunkel, R. et al., (1992) *Anal. Chem.* 62, 3133–3149; Harper, J. K. et al., (1996) *J. Chem. Soc. perkin Trans.* 2, 91–100). The INADEQUATE analysis confirmed all but three bonds at greater than a 99.9% confidence level. Thus, this very powerful technique unequivocally confirms all of the structural conclusions.

Thus, oocydin A is a chlorinated macrocyclic lactone having a tetrahydrofuran ring internal to it with a side chain terminated with a carboxylic acid functionality. The structure shown in FIG. 1 is consistent with all of the spectral information obtained. Although several asymmetric centers are present in the molecule, only the relative stereochemistry is presented and no absolute stereochemistry is implied. Oocydin A is one of only a few macrocyclic lactones that have ever been isolated. Others including the fijinolides and the laulimalides have been isolated from marine animals, and demonstrate general toxic activity to various biological systems.

Bioassays. A simple plate bioassay test was used to detect bioactivity of various fractions in the purification of oocydin. Aliquots (10–20 µl) of sample were placed on a PDA plate, dried by placement under a hood having positive airflow, and then inoculated with 0.5×0.5 cm plugs of agar containing *P. ultimum*. The agar plugs were placed in each of the quadrants of the plate and then incubated for 36–48 hr at 23 C. Antioomycetous activity was apparent as a zone of growth inhibition.

The antioomycetous activity of pure oocydin A was also tested against a series of plant pathogens by dissolving 50 µg of oocydin A in 100 µl$^{-1}$ in methanol and spotting 10 µl portions on to PDA plates and allowing the droplets to dry. Each plate was overlaid or sprayed with an aqueous suspension of the test fungus in water (containing mycelial fragments and/or spores) and the plate sealed with a piece of parafilm and then incubated at 23° C. for 4–5 day. In each case, a positive control test was also conducted (the residue obtained from the methylene chloride extracted medium without the bacterium).

Minimum inhibitory concentrations (MICs) of oocydin A against various phycomycetes were determined by preparing a stock solution of oocydin A (1 mg ml$^{-1}$ in methanol. This solution was dispensed, by serial 2-fold dilution, into a 24-well plate. Each well of the plate contained 500 µl of PD broth. A small plug of the test fungus was placed into each well and the plate incubated for 48–72 hr at 23° C. The MIC was taken as the concentration of oocydin A in the well where no growth visually appeared after either 48 hr or 72 hr.

The Phytophthora spp. Weed the most sensitive Oomycetes with MICs of approximately 0.03 µg ml$^{-1}$ (TABLE 1). *Pythium ultimum* was less sensitive than the Phytophthora spp.

TABLE 1

The Effects of Oocydin on Various Phytopathogenic Oomycetes.

| Oomycete Tested | Oocydin MIC µg ml$^{-1}$ Test 1 | Test 2 | Metalaxyl MIC µg ml$^{-1}$ |
|---|---|---|---|
| *Pythium ultimum* | 0.11 | 0.39 | ND |
| *Phytophthora parasitica* | 0.03 | 0.05 | 0.06 |
| *Phytophthora cinnamomi* | 0.03 | 0.02 | 0.06 |
| *Phytophthora citrophora* | 0.03 | 0.02 | ND |

ND = no determination

When tested on PDA plates (5.0 µg oocydin A applied to a localized agar surface in a droplet of methanol; thus at 5.0 µg ml$^{-1}$ or greater) against a group of organisms representing 3 classes of fungi, oocydin A showed little or no activity. For instance, against *Geotrichum candidum* (Fungi Imperfecti) it was inactive; likewise only slight inhibition of growth was observed for *Sclerotinia sclerotiorum* (Ascomycete) and *Rhizoctonia solani* (Basidiomycete). In other plate tests, no activity was noted against either *Verticillum dahliae*, or *Alternaria tomato*.

Oocydin A was tested against several important fungal pathogens of humans using the MIC microwell plate assay. MIC tests were conducted using the microbroth dilution assay as recommended by the subcommittee on antifungal susceptibility testing of the U.S. National Committee for Clinical Laboratory Standards (NCCLS). The effects of the well-established antimycotics metalaxyl (N-(2,6-dimethylphenyl)-N-(methoxyacetyl)-DL-alanine methyl ester), pseudomycin B and amphotericin B were determined concomitantly. At concentrations up to 80 µg ml$^{-1}$ oocydin A had no effect on *Candida albicans, Cryptococcus neoformans, Aspergillus fumigatus, Candida parapsilosis,* or *Histoplasma capsulatum*. However, with the exception of *A. fumigatus*, pseudomycin B inhibited growth of all of these organisms with MICs <1.0 µg ml$^{-1}$ and all of these fungi were sensitive to amphotericin B with MICs <1.0 µg ml$^{-1}$.

Oocydin A was tested also against human cancer cell lines BT-20, MCF 7 (American Type Culture Collection, Bethesda, Md., USA) and compared with activity against a normal human mammary human cell line (cc2551 HMEC from Clonetics, San Diego, Calif., USA). These cells were exposed to serial dilutions of oocydin A. After 3 days of exposure, the cells were stained with neutral red and the absorbance measured at 540 nm. For non-adherent cells a modification of the staining protocol of Berent, S. L. et al., (1986) *Nucleic Acid Res* 14, 8997–9015 was used. The results were recorded as IC$_{50}$ values.

Oocydin A appears to have selective toxicity against various human cell lines. In preliminary studies, IC$_{50}$ values of 0.2 µg m$^{-1}$ against BT-20 (breast cancer cell line), 0.42 µg ml$^{-1}$ against MCF-7 (breast cancer cell line), and 0.6 µg ml$^{-1}$ against a normal mammary cell line were noted.

The foregoing description has been presented only for the purposes of illustration and is not intended to limit the invention to the precise form disclosed, but by the claims appended hereto.

We claim:

1. A composition of matter comprising isolated oocydin A, wherein the isolated oocydin A is of the following formula:

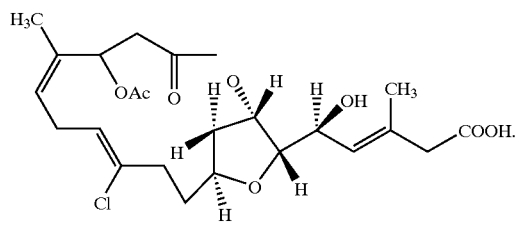

2. The composition of claim 1, further comprising Prodigiosin.

3. The composition of claim 1, comprising a culture medium in which *Serratia marcescens* MSU-97 has been cultured.

4. An anti-oomycetes composition comprising the isolated oocydin A of claim 1.

5. An antifungal comprising the isolated oocydin A of claim 1.

6. The composition of claim 1, further comprising an agriculturally acceptable carrier.

7. The composition of claim 1, further comprising an agriculturally beneficial agent.

8. The composition of claim 7, wherein the agriculturally beneficial agent is a fertilizer.

* * * * *